(12) United States Patent
Wang et al.

(10) Patent No.: US 8,242,282 B2
(45) Date of Patent: Aug. 14, 2012

(54) HISTONE DEACETYLASE INHIBITORS

(75) Inventors: Hui-po Wang, Taipei (TW); On Lee, Hsin-Chu (TW); Yu-Wen Cheng, Taipei (TW); Chun-li Wang, Pingzhen (TW); Feng-Shuo Chang, Banqiao (TW); Hsiao Che-Chih, Shenkeng Township (TW)

(73) Assignee: Taipei Medical University, Taipei (TW)

( * ) Notice: Subject to any disclaimer, the term of this patent is extended or adjusted under 35 U.S.C. 154(b) by 176 days.

(21) Appl. No.: 12/781,979

(22) Filed: May 18, 2010

(65) Prior Publication Data

US 2011/0288133 A1 Nov. 24, 2011

(51) Int. Cl.
C07D 213/00 (2006.01)
A61K 31/44 (2006.01)

(52) U.S. Cl. ......... 546/329; 514/345

(58) Field of Classification Search .......... None
See application file for complete search history.

(56) References Cited

FOREIGN PATENT DOCUMENTS

| GB | 1 171 670 | 11/1969 |
|----|-----------|---------|
| WO | 2005/037257 | 4/2005 |
| WO | 2011/028309 | 3/2011 |
| WO | 2011/084991 | 7/2011 |

OTHER PUBLICATIONS

Silverman, R. "The Organic Chemistry of Drug Design and Drug Action," 2004, Elsevier, pp. 29-32.*
CAPLUS 1995:440488.*
Salisbury and Cravatt "Optimization of activity-based probes for proteomic profiling of histone deacetylase complexes"; J.Am. Chem. Soc. 2008, 130, 2184-2194.
Wittich et al. "Structure-activity relationships on phenylalanine-containing inhibitors of histone deacetylase: in vitro enzyme inhibition, induction of differentiation, and inhibition of proliferation in friend leukemic cells"; J. Med. Chem. 2002, 45, 3296-3309.
Schafer et al. "Phenylalanine-containing hydroxamic acids as selective inhibitors of class IIb histone deacetylases (HDACs)" Bioorganic & Medicinal Chemistry, 2008, 16, 2011-2033.
Schafer et al. "Pyridylalanine-containing hydroxamic acids as selective HDAC6 inhibitors"; CheckMedChem 2009, 4, 283-290.
Tischler, Jessica L. et al: "Simple inhibitors of histone deacetylase activity that combine features of short-chain fatty acids and hydroxamic acid inhibitors", Journal of Enzyme Inhibition and Medicinal Chemistry, 23(4), pp. 549-555, 2008, XP000002658614.
Conejo-Garcia A et al: "A prodrug system for hydroxylamines based on esterase catalysis", Bioorganic & Medicinal Chemistry Letters, vol. 15, No. 18, Sep. 15, 2005, pp. 4004-4009, XP027388675.
T. Kurz et al: "o-Protected 3-hydroxy-oxazolidin-2, 4-diones: novel precursores in the synthesis of alpha-hydroxyhydroxamic acids", Organic & Biomolecular Chemistry, vol. 2, No. 14, 2004, pp. 2023-2027, XP000002658615.
Danieli, B. et al: "New photochemical synthesis of lactones", Chimica E L'Industria (Milan, Italy), 50(5), 553-5, 1968, XP000002658616.
Potapov, V. M. et al: "Synthesis of arylalkylhydroxamic acids with an .alpha.-asymmetric carbon atom", Zhurnal Organicheskoi Khimii, 18(6), 1982, XP000002658617.
Zhang Y. et al: "Design, synthesis and preliminary activity assay of 1,2,3,4-tetrahydroisoquinoline-3-carboxylic acid derivatives as novel Histone deacetylases (HDACs) inhibitors", Bioorganic & Medicinal Chemistry, vol. 18, No. 5, Mar. 1, 2010, pp. 1761-1772, XP026925748.

* cited by examiner

Primary Examiner — Janet Andres
Assistant Examiner — Heidi Reese
(74) Attorney, Agent, or Firm — Occhiuti Rohlicek & Tsao LLP

(57) ABSTRACT

This invention relates to compounds of the following general formula:

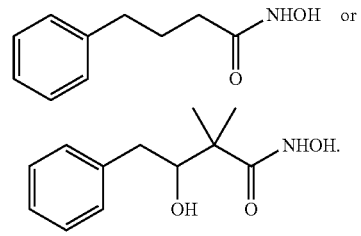

The variables are defined herein. Also disclosed is a method for treating mucositis or cancer using these compounds.

23 Claims, No Drawings

HISTONE DEACETYLASE INHIBITORS

BACKGROUND

Histone deacetylases (HDACs) are a class of enzymes that regulate histone acetylation and thereby regulate gene expression.

HDAC inhibitors have been known to induce cell growth arrest, differentiation, and apoptosis in tumor cells. See, e.g., Lu et al., *J. Med. Chem.* 2005, 48, 5530-5535; Kulp et al., *Clin. Cancer Res.* 2006, 12, 5199-5206; and Ryan et al., *J. Clin. Oncol.* 2005, 23, 3912-3922. It has also been reported that they attenuate inflammation (e.g., mucositis induced by chemotherapy or radiotherapy) via suppressing the expression of pro-inflammatory cytokines See, e.g., I. M. Adcock, British Journal of Pharmacology, 2007, 150(7): 839-831; and Y. L. Chung et al., Carcinogenesis 2009 30(8): 1387-1397.

HDAC inhibitors are currently attracting great attention as potential anti-cancer and anti-inflammation agents.

SUMMARY

This invention is based on a discovery that certain amino-containing compounds are effective HDAC inhibitors and have potent anti-mucositis activity. Thus, this invention relates to amino-containing compounds and their use in treating HDAC-related diseases.

In one aspect, this invention features compounds of formula (I):

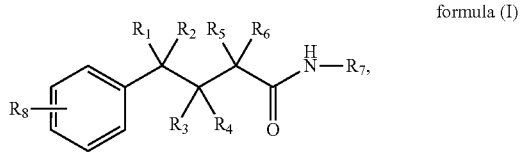

formula (I)

in which each of $R_1$, $R_2$, $R_3$, $R_4$, $R_5$, and $R_6$, independently, is H, alkyl, OH, or alkoxy; $R_7$ is OH, OR, or OC(O)R, R being alkyl optionally substituted with halo, aryl, heteroaryl, amino, or carboxyl; and $R_8$ is H, $(CH_2)_m NHC(O)R'$, or $(CH_2)_m OC(O)R'$, m being 0, 1, or 2, and R' being alkyl optionally substituted with halo, aryl, heteroaryl, amino, or carboxyl.

Referring to formula (I), a subset of the compounds described above may have one or more of the following features: $R_7$ is OC(O)R, R being alkyl substituted with $NH_2$ or phenyl; and each of $R_1$, $R_2$, $R_3$, $R_4$, $R_5$, and $R_6$ is H, or each of $R_1$, $R_2$, and $R_3$ is H, $R_4$ is OH, and each of $R_5$ and $R_6$ is alkyl.

In another aspect, this invention features compounds of formula (II):

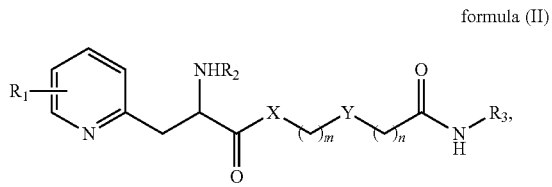

formula (II)

in which $R_1$ is H, OH, amino, alkoxy, arylalkoxy (e.g., benzyloxy), alkylcarbonyloxy, or alkoxycarbonyloxy; $R_2$ is H, OH, alkoxy, alkylcarbonyl, or alkoxycarbonyl; $R_3$ is OH or phenyl; X is O or NH; Y is phenylene or —$CH_2$—; and each of m and n, independently, is 0, 1, 2, 3, 4, or 5.

Referring to formula (II), a subset of the compounds described above may have one or more of the following features: X is NH or O, Y is phenylene or —$CH_2$—, m is 0, n is 3, $R_1$ is OH or alkoxy, and $R_3$ is OH.

In another aspect, this invention features compounds of formula (III):

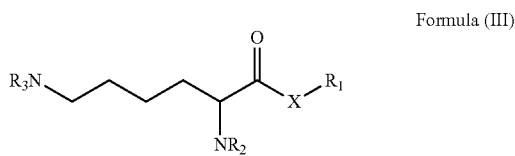

Formula (III)

wherein X is O or NH; $R_1$ is OH, alkyl, or aryl; and one of $R_2$ and $R_3$ is C(O)OR, R being alkyl, alkenyl, or aryl, and the other is H or C(O)OR', R' being alkyl, alkenyl, or aryl.

Referring to formula (III), a subset of the compounds described above may have one or more of the following features: X is O or NH, $R_1$ is $CH_2Ph$ or OH, and each of $R_2$ and $R_3$ is (t-butyloxy)carbonyl (Boc) or (9-fluorenylmethyl)carbonyl (Fmoc).

The term "alkyl" refers to a straight, branched, or cyclic monovalent hydrocarbon containing, unless otherwise stated, 1-20 carbon atoms (e.g., $C_1$-$C_{10}$). Examples of alkyl include, but are not limited to, methyl, ethyl, n-propyl, i-propyl, n-butyl, i-butyl, t-butyl, or cyclohexyl. Alkyl may also contain one or more heteroatoms (such as O, N, S, or Se) and/or one or more double or triple bonds. The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, tetrazol, and thiazolyl.

Alkyl, aryl, and heteroaryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)$NH_2$), carboxyl (—COOH), and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "amino" refers to $NH_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl.

The compounds described herein include the compounds themselves, as well as their salts, their solvates, and their prodrugs, if applicable. A salt, for example, can be formed between an anion and a positively charged group (e.g., amino) on a compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an indolyl or indolinyl hydroxamate compound. Suitable cations include sodium ion, potassium ion, magnesium ion, calcium ion, and an ammonium cation such as tetramethylammonium ion. The compounds described above also include those salts containing quaternary nitrogen atoms. Examples of prodrugs include esters and other pharmaceutically acceptable derivatives, which, upon administration to a subject, are capable of providing active compounds described above.

Shown below are exemplary compounds described herein:

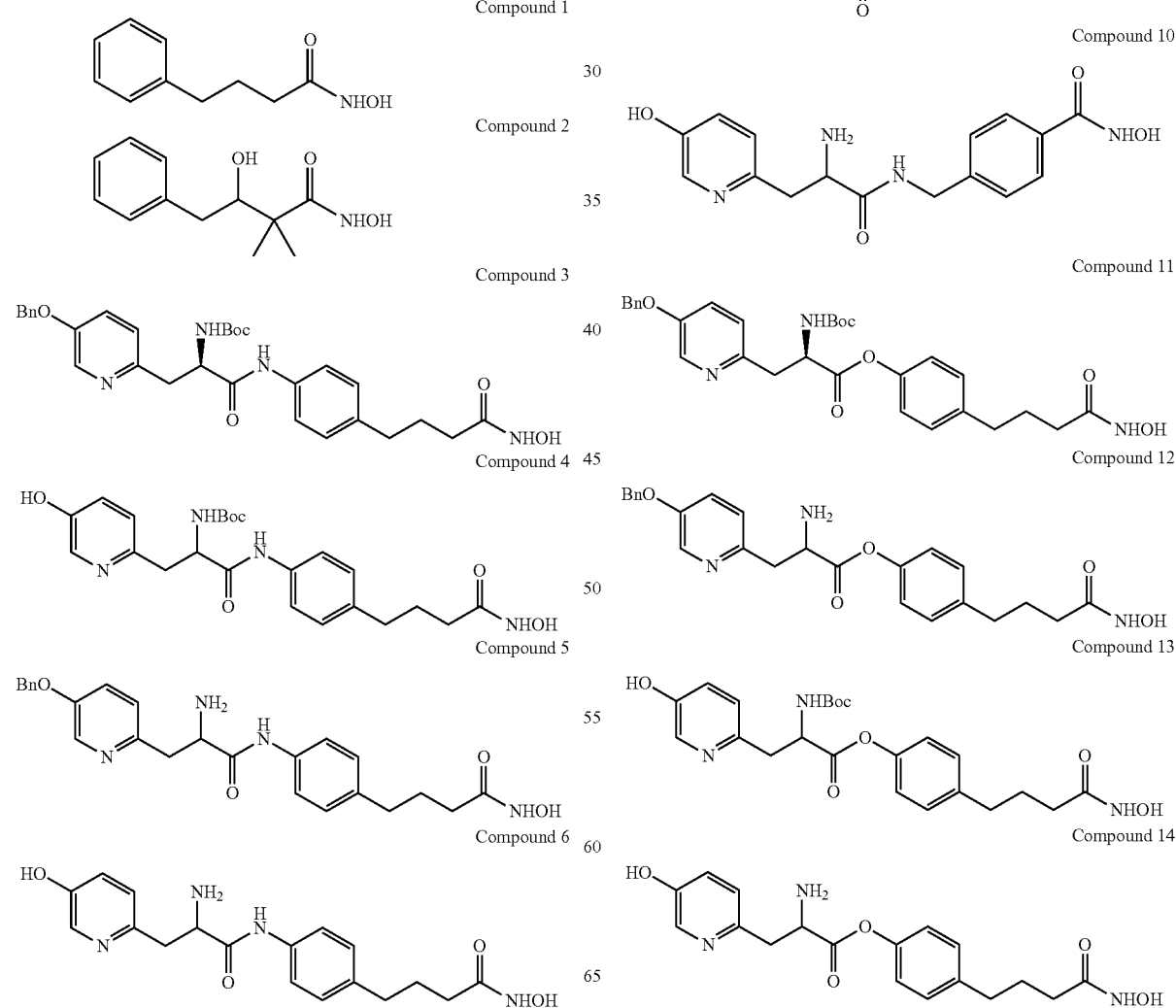

-continued

Compound 15

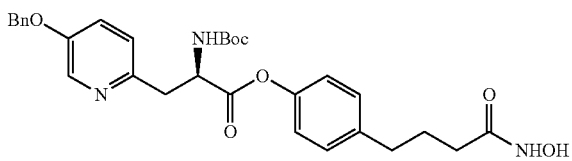

In still another aspect, this invention relates to a method for inhibiting HDAC activity by contacting a cell with an effective amount of one of the compounds described above.

In yet another aspect, this invention relates to a method for treating mucositis or cancer by administering to a subject in need thereof an effective amount of one of the above-described compounds.

Also within the scope of this invention is a pharmaceutical composition containing one or more of these compounds for use in treating mucositis or cancer, as well as these therapeutic uses and use for the manufacture of a medicament for treating mucositis or cancer.

The details of one or more embodiments of the invention are set forth in the description below. Other features, objects, and advantages of the invention will be apparent from the description and the claims.

DETAILED DESCRIPTION

The compounds of this invention can be synthesized by well-known methods. For example, Compounds 1-15 described above can be prepared by modifying phenylbutyric acid, lysine, or azatyrosine via conventional chemical transformations (including using protecting groups), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Compounds thus synthesized can be further purified by flash column chromatography, high performance liquid chromatography, crystallization, or any other suitable methods.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the compounds of this invention and a pharmaceutically acceptable carrier, and (2) a method for treating mucositis or cancer by administering to a subject in need of this treatment an effective amount of this compound.

As used herein, the term "treating" refers to administering an active compound to a subject that has mucositis or cancer, or has a symptom of or a predisposition toward it, with the purpose to cure, heal, alleviate, relieve, alter, remedy, ameliorate, improve, affect, or reduce the risk of the disorder, the symptoms of or the predisposition toward the mucositis or cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Mucositis is inflammation and ulceration of the mucous membranes lining the digestive tract, usually as an adverse effect of chemotherapy and radiotherapy. It can occur in the mouth or anywhere along the gastrointestinal tract.

Cancer includes both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A composition containing one of the compounds of this invention also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the compounds of this invention can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the compounds of this invention in inhibiting HDACs. The effective compounds can further be examined for their efficacy in treating mucositis and cancer either in vitro or in vivo. For example, a compound can be administered to an animal (e.g., a mouse model) having mucositis or cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Chemical Syntheses

1. Synthesis of N-hydroxy-4-phenylbutanamide (Compound 1)

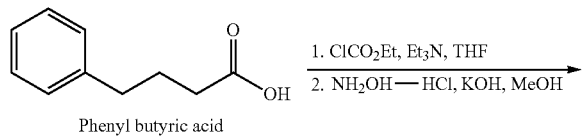

Phenyl butyric acid

Compound 1

A solution of 4-phenylbutyric acid (10.0 g, 60.9 mmol) in anhydrous THF (180 mL) was added ethyl chloroformate (7.0 mL, 73.1 mmol) and triethylamine (11.1 mL, 79.2 mmol) at 0° C. The mixture was stirred at 0° C. for 15 min. The solid was filtered off. The filtrate was added to a freshly prepared methanolic hydroxylamine solution (63.0 mL, prepared by adding 6.34 g or 91.4 mmol of hydroxylamine hydrochloride to 30.0 mL of a stirred methanolic solution containing 5.13 g or 91.4 mmol of KOH at 0° C. for 15 min). The resulting mixture was stirred at room temperature for 30 min and evaporated in vacuo. The residue was purified by chromatography to give Compound 1 (6.4 g, 58%): mp>300° C.; NMR (400 MHz in CDCl$_3$): δ 1.98 (m, 2H, PhCH$_2$—CH$_2$—CH$_2$CONHOH), 2.13 (t, 2H, Ph-CH$_2$—CH$_2$CH$_2$CONHOH), 2.64 (t, 2H, PhCH$_2$CH$_2$—CH$_2$—CONHOH), 7.15 (d, 2H, Ar—H), 7.20 (t, 2H, Ar—H), 7.28 (m, 1H, Ar—H), 8.20 (br, 1H, NH).

2. Synthesis of N,3-dihydroxy-2,2-dimethyl-4-phenylbutanamide (Compound 2)

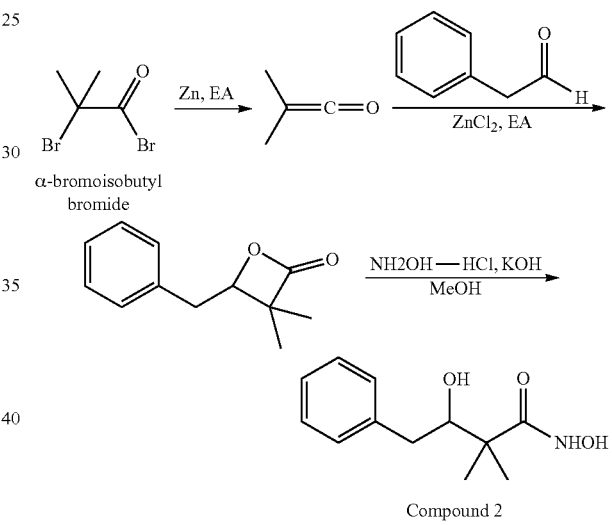

α-bromoisobutyl bromide

Compound 2

Zinc (0.85 g, 16.0 mmol) and ethylacetate (10.0 mL) were added to a Wolff bottle equipped with a distillation apparatus. The mixture was heated at 40° C. To this was slowly added α-bromoisobutyl bromide (3.45 g, 16.0 mmol). 2-Methylprop-1-en-1-one was collected below 34° C. as a yellow liquid.

2-Methylprop-1-en-1-one (0.04 g, 5.0 mmol) and 2-phenylacetaldehyde (0.60 g, 5.0 mmol) were dissolved in ethylacetate (3.5 mL) and stirred at 0° C. under nitrogen. Zinc(II) chloride (0.03 g, 0.25 mmol) was added quickly and the reaction mixture was kept at 0° C. for a short period and then at room temperature overnight (monitored by TLC). The reaction mixture was then treated at room temperature with a solution of NaHCO$_{3(aq)}$. The organic layers were combined, dried, and concentrated in vacuo, and the crystallization in CH$_2$Cl$_2$:hexane=1:1 gave 4-benzyl-3,3-dimethyloxetan-2-one (0.80 g, 84%).

4-Benzyl-3,3-dimethyloxetan-2-one (0.95 g, 5.0 mmol) was dissolved in the MeOH (2.0 mL) and stirred under nitrogen at 0° C. To this was added a solution of hydroxylamine-hydrochloride (0.07 g, 10 mmol) and potassium hydroxide (0.06 g, 10.0 mmol) in MeOH (40.0 mL). The reaction mixture was stirred at room temperature and monitored by TLC. The reaction mixture was concentrated in vacuo to give crude Compound 2 (0.86 g, 77%) as solid. mp 95-96° C.; NMR (400 MHz in CDCl$_3$, Bruker AVANCE-400): δ 1.31 (s, 3H, CH$_3$), 1.32 (s, 3H, CH$_3$), 2.55 (dd, 1H, J=10.0 Hz, CH$_2$), 2.82 (dd, 1H, J=1.8 Hz, CH$_2$), 3.95 (dd, 1H, J=2.1 Hz), 6.36 (br, 1H, OH), 7.23-7.25 (m, 3H, Ar—H), 7.30-7.33 (m, 2H, Ar—H).

3. Synthesis of (R)-tert-butyl 3-(5-(benzyloxy)pyridin-2-yl)-1-(4-(4-(hydroxylamino)-4-oxobutyl)phenylamino)-1-oxopropan-2-ylcarbamate (Compound 3)

(i) Synthesis of a mixture of methyl 4-(4-nitrophenyl)butanoate and methyl 4-(2-nitrophenyl)butanoate A mixture of 4-(p-Nitrophenyl)butyric acid and 4-(o-Nitrophenyl) butyric acid (3.22 g, 15.38 mmol) in HCl-saturated methanol (60 mL) was refluxed for 12 h (monitored by TLC). After evaporation of the solvent, the residue was dissolved in 50 mL dichloromethane and washed with saturated Na$_2$CO$_3$. The dichloromethane solution was separated, dried over magnesium sulfate, and concentrated in vacuo to give the title compound (3.43 g, 100%).

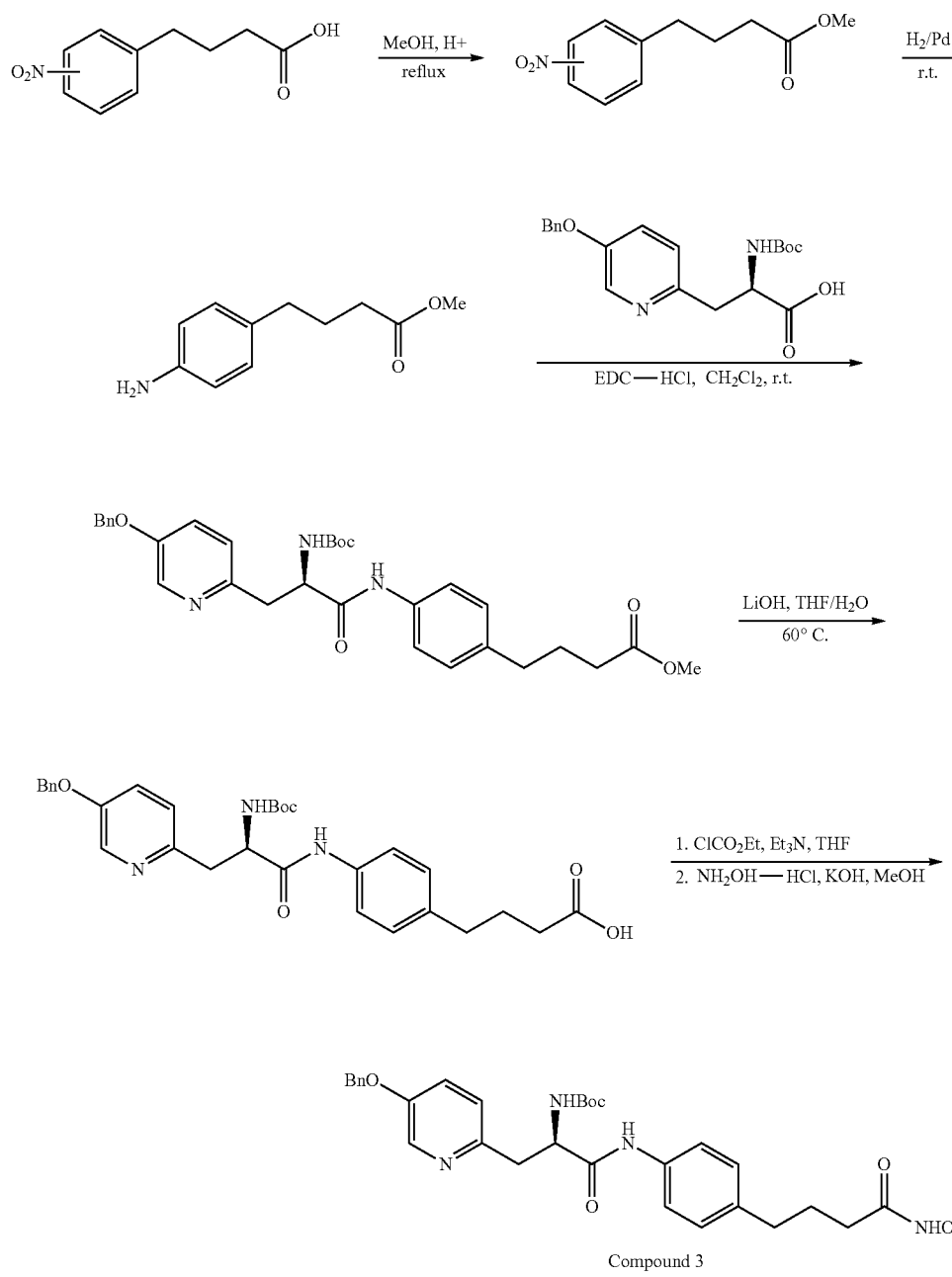

Compound 3

(ii) Synthesis of methyl 4-(4-aminophenyl)butanoate

A mixture of methyl 4-(4-nitrophenyl)butanoate and methyl 4-(2-nitrophenyl)butanoate (2.24 g, 10.03 mmol) and 0.2 g of 10% Pd/C in 40 mL of methanol was vigorously stirred under hydrogen air. The mixture was stirred for 4 h at room temperature (monitored by TLC), and filtered through Celite. The solvent was evaporated. The residue was purified by chromatography to give the title compound (0.80 g, 41%): NMR (400 MHz in CDCl$_3$, Bruker AVANCE-400): δ 1.89 (m, 2H, CH$_2$), 2.31 (t, 2H, CH$_2$—CH$_2$—COOMe), 2.53 (t, 2H, CH$_2$), 3.58 (br, 2H, NH$_2$), 3.65 (s, 3H, OMe), 6.61 (d, 2H, J=3.5 Hz, Ar—H), 6.95 (d, 2H, J=3.4 Hz).

(iii) Synthesis of (R)-methyl 4-(4-(3-(5-(benzyloxy)pyridin-2-yl)-2-(tert-butoxycarbonylamino)propanamido)phenyl)butanoate A mixture of methyl methyl 4-(4-aminophenyl)butanoate (1.24 g, 6.42 mmol), 3-(5-(benzyloxy)pyridine-2-yl)-2-(tert-butoxycarbonylamino) propanoic acid (2.17 g, 5.84 mmol), and 1-ethyl-3-(3-dimethyllaminopropyl) carbodiimide hydrochloride (1.12 g, 5.84 mmol) in 25 mL dichloromethane was stirred at room temperature for 2 h (monitored by TLC). The mixture was washed with water and dried over magnesium sulfate. The residue was purified by chromatography (EA:Hex=1:1) to give the title compound (2.37 g, 74%). mp 166-167° C.; (400 MHz in CDCl$_3$, Bruker AVANCE-400): δ 1.31 (s, 9H, Boc), 1.93 (m, 2H, CH$_2$), 2.30 (t, 2H, CH$_2$—CH$_2$—COOMe), 2.59 (t, 2H, CH$_2$), 3.22 (m 2H, CH$_2$), 3.66 (s, 3H, OMe), 4.43 (t 1H CH) 5.13 (s 2H OBn), 6.97 (d, 2H, J=7.9 Hz, Ar—H), 7.09 (d, 1H, J=8.0 Hz, Pyr-H), 7.20~7.48 (m, 9H Ar—H), 8.26 (br, 1H, NH), 9.91 (br, 1H, NH).

(iv) Synthesis of (R)-4-(4-(3-(5-(benzyloxy)pyridin-2-yl)-2-(tert-butoxycarbonylamino)propanamido)phenyl)butanoic acid A mixture of methyl 4-(4-(3-(5-(benzyloxy)pyridin-2-yl)-2-(tert-butoxycarbonylamino)propanamido)phenyl)butanoate (0.59 g, 1.07 mmol) and lithium hydroxide (0.26 g, 10.7 mmol) in 10 mL THF/H$_2$O (1:1) was heated at 60° C. for 2 h (monitored by TLC). The solution was acidified to PH=2 and extracted with dichloromethane. The dichloromethane was separated, dried over magnesium sulfate, and concentrated in vacao to give 0.51 g of the desired compound (90%): (400 MHz in CDCl$_3$, Bruker AVANCE-400): δ 1.30 (s, 9H, Boc), 1.74 (m, 2H, CH$_2$), 2.17 (t, 2H, CH$_2$—CH$_2$—COOMe, J=7.34 Hz), 2.52 (t, 2H, CH$_2$, J=7.55 Hz), 2.92-3.07 (m, 2H, CH$_2$), 4.44 (m, 1H CH), 5.13 (s, 2H OBn), 7.09 (d, 1H, J=8.47 Hz, Ar—H), 7.21 (d, 1H, Ar—H, J=8.52 Hz), 7.31~7.48 (m, 9H Ar—H), 8.26 (br, 1H, NH), 9.91 (br, 1H, OH).

(v) Synthesis of (R)-tert-butyl 3-(5-(benzyloxy)pyridin-2-yl)-1-(4-(4-(hydroxyl-amino)-4-oxobutyl)phenylamino)-1-oxopropan-2-ylcarbamate (Compound 3)

To a solution of 4-(4-(3-(5-(benzyloxy)pyridine-2-yl)-2-(tert-butoxycarbonylamino) propanamido)phenyl)butanoic acid in anhydrous THF (0.43 g, 0.80 mmol) was added ethyl chloroformate (0.1 mL, 0.88 mmol) and triethylamine (0.15 mL, 0.96 mmol) at 0° C. The mixture was stirred at 0° C. for 30 min. The solid was filtered off and the filtrate was added to a hydroxylamine MeOH solution, which was freshly prepared by adding a solution of hydroxylamine hydrochloride (0.11 g, 1.60 mmol) in MeOH (1.1 mL) to a stirred solution of KOH (0.09 g, 1.60 mmol) in MeOH (0.5 mL) at 0° C. After stirring for 15 min, the precipitate was removed and the filtrate was stirred at room temperature for 30 min (monitored by TLC) and evaporated in vacuo. The residue was extracted with EA/H$_2$O and recrystallized in MeOH/Ether to give compound 3 (0.3 g, 74%). mp>300° C.; NMR (400 MHz in CDCl$_3$, Bruker AVANCE-400): δ 1.23 (s, 9H, Boc), 1.75 (m, 2H, CH$_2$), 1.93 (t, 2H, CH$_2$—CH$_2$—CONHOH, J=7.0 Hz), 2.51 (t, 2H, CH$_2$, J=6.5 Hz), 2.95 (m, 2H, CH), 4.45 (m, 1H, CH), 5.14 (s, 2H, OBn), 6.97 (d, 1H, J=8.0 Hz, Ar—H), 7.09 (d, 2H, J=8.5 Hz), 7.21 (d, 1H, J=8.5 Hz, Ar—H), 7.32-7.47 (m, 8H, Ar—H), 8.26 (br, 1H, NH), 8.62 (br, 1H, NH), 9.91 (br, 1H, NH), 10.32 (br, 1H, OH).

4. Synthesis of tert-butyl-1-(4-(4-(hydroxyamino)-4-oxobutyl)phenylamino)-3-(5-hydroxypyridin-2-yl)-1-oxopropan-2-ylcarbamate (Compound 4)

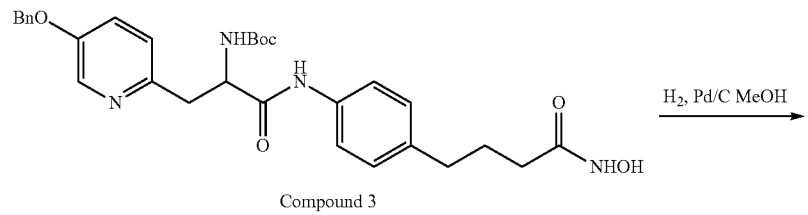

Compound 3

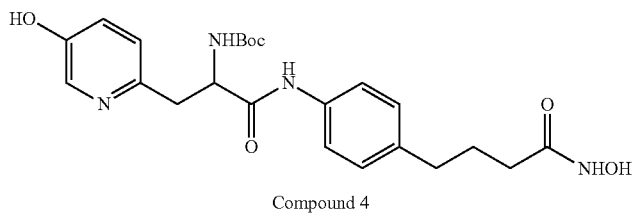

Compound 4

A mixture of tert-butyl 3-(5-(benzyloxy)pyridin-2-yl)-1-(4-(4-(hydroxyamino)-4-oxobutyl)phenylamino)-1-oxopropan-2-ylcarbamate (0.1 g, 0.19 mmol) and 10 mg of 10% Pd/C in 2 mL of methanol was vigorously stirred under $H_2$ for 4 h at room temperature (monitored by TLC). It was filtered through Celite. The solvent was evaporated. The residue was purified by chromatography to give Compound 4 (0.09 g, 89%). Mp: 166-167° C.; NMR (400 MHz in $CDCl_3$, Bruker AVANCE-400): δ 1.31 (s, 9H, Boc), 1.75 (m, 2H, $CH_2$), 1.93 (t, 1H, $CH_2$, J=7.10 Hz), 2.52 (t, 2H, $CH_2$, J=7.10 Hz), 2.94 (m, 2H, $CH_2$), 4.41 (m, 1H, CH), 6.94 (d, 1H, Ar—H, J=7.99 Hz), 7.05 (m, 1H, Ar—H), 7.08 (d, 2H, Ar—H, J=7.88 Hz), 7.21 (m, 1H, Ar—H), 7.46 (d, 2H, Ar—H, J=8.15 Hz), 8.03 (br, 1H, NH), 9.88 (br, 1H, NH), 10.32 (br, 1H, OH).

5. Synthesis of 4-(4-(2-amino-3-(5-(benzyloxy)pyridin-2-yl)propanamido) phenyl)-N-hydroxybutanamide (Compound 5)

t-Butyl 3-(5-(benzyloxy)pyridin-2-yl)-1-(4-(4-(hydroxyamino)-4-oxobutyl)-phenylamino)-1-oxopropan-2-yl-carbamate (0.1 g, 0.19 mmol) was dissolved in DCM/TFA (v/v=1:1) (30 mL), and stirred at room temperature for 4 h (monitored by TLC). The solution was evaporated in vacuo to give Compound 5 (0.062 g, 61%). mp>300° C.; NMR (400 MHz in $CDCl_3$, Bruker AVANCE-400): δ 1.75 (m, 2H, $CH_2$), 1.95 (t, 2H, $CH_2$, J=7.37 Hz), 2.52 (t, 2H, $CH_2$, J=7.55 Hz), 3.16 (m, 2H, $CH_2$), 4.30 (m, 1H, CH), 5.16 (s, 2H, OBn), 7.13 (d, 2H, Ar—H, J=8.06 Hz), 7.24 (d, 1H, Ar—H, J=8.47 Hz), 7.33-8.46 (m, 9H, Ar—H), 8.22 (br, 2H, $NH_2$), 8.30 (m, 1H, NH), 8.64 (br, 1H, NH), 10.33 (br, 1H, OH), 10.36 (br, 1H, TFA).

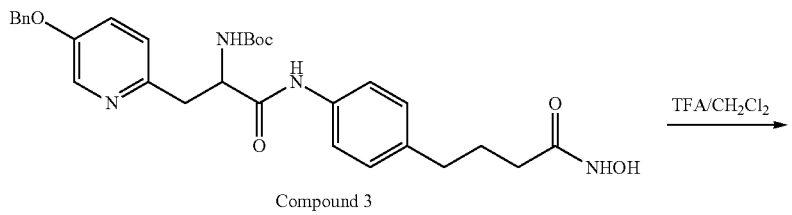

Compound 3

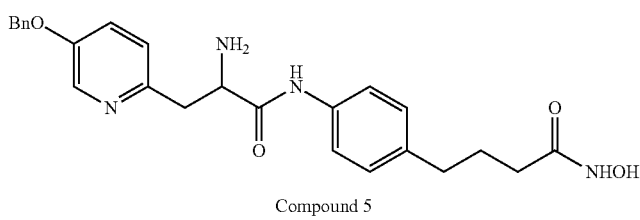

Compound 5

6. Synthesis of 4-(4-(2-amino-3-(5-hydroxypyridin-2-yl)-propanamido) phenyl)-N-hydroxybutanamide (compound 6)

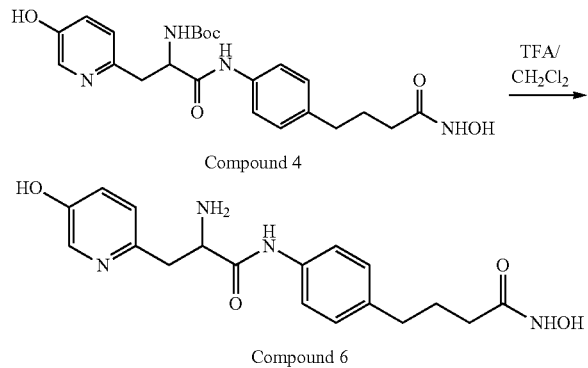

t-Butyl 1-(4-(4-(hydroxyamino)-4-oxobutyl)phenylamino)-3-(5-hydroxypyridin-2-yl)-1-oxopropan-2-ylcarbamate (0.10 g, 0.19 mmol) was dissolved in 10 mL of TFA and 10 mL of $CH_2Cl_2$ and stirred for 4 h at room temperature (monitored by TLC). The solvent was evaporated. The residue was purified by chromatography to give Compound 6 (0.51 g, 64%): mp 230° C. decp; (400 MHz in $CDCl_3$, Bruker AVANCE-400): δ 1.77 (m, 2H, $CH_2$), 2.20 (t, 2H, $CH_2$, J=7.01 Hz), 2.51 (t, 2H, $CH_2$, J=8.27 Hz), 3.43 (m, 2H, $CH_2$), 4.48 (m, 1H, CH), 7.13 (d, 1H, Ar—H, J=8.19 Hz), 7.26-7.32 (m, 4H, Ar—H), 7.51 (d, 1H, Ar—H, J=8.07 Hz), 7.61 (m, 1H, Ar—H), 8.39 (br, 1H, NH), 8.65 (br, 2H, $NH_2$), 10.44 (br, 1H, OH), 11.04 (br, 1H, TFA).

7. Synthesis of tert-butyl 3-(5-(benzyloxy)pyridin-2-yl)-1-(4-(hydroxycarbamoyl)benzylamino)-1-oxopropan-2-ylcarbamate (Compound 7)

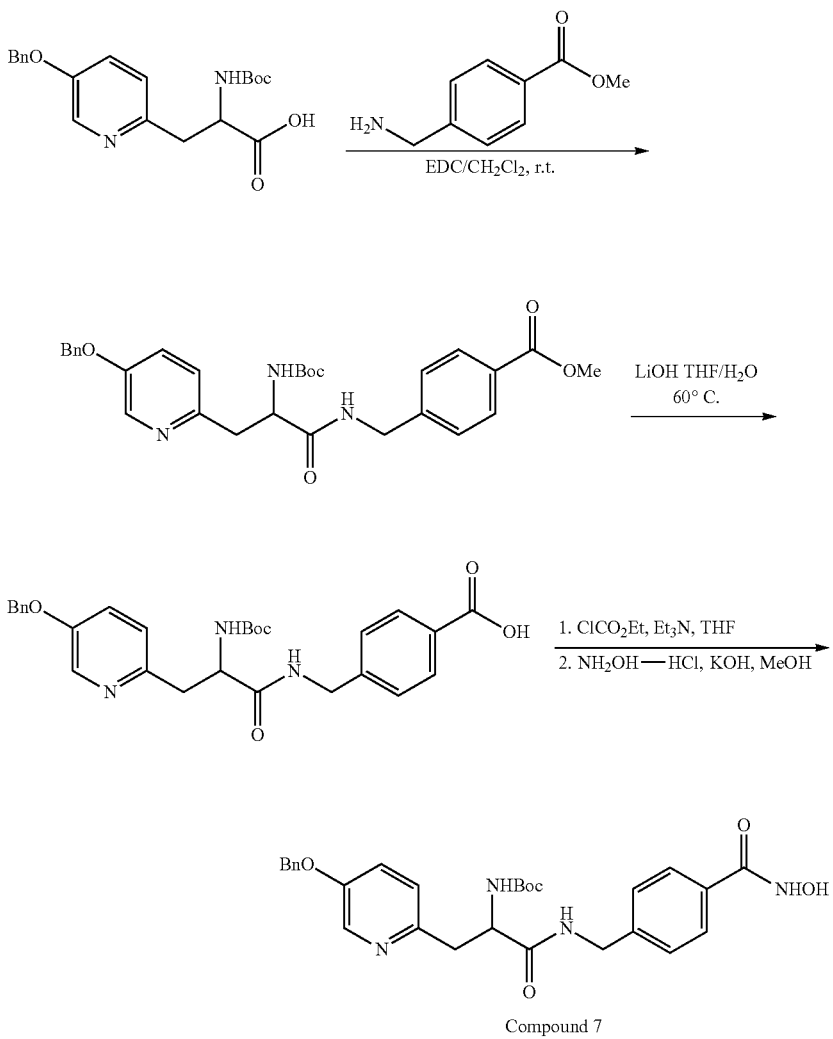

(i) Synthesis of methyl 4-((3-(5-(benzyloxy)pyridin-2-yl)-2-(tert-butoxycarbonylamino)propanamido)methyl)benzoate A mixture of methyl 4-(aminomethyl)benzoate (2 g, 10 mmol), 3-(5-(benzyloxy)-pyridine-2-yl)-2-(tert-butoxycarbonylamino) propanoic acid (1.04 g, 11 mmol), and 1-ethyl-3-(3-dimethyllaminopropyl)carbodiimide hydrochloride (2 g, 10.4 mmol) in 50 mL dichloromethane was stirred at room temperature for 2 h (monitored by TLC). The mixture was extracted with water and dried over magnesium sulfate. The residue was purified by chromatography (EA:Hex=1:1) to give the title compound (1.5 g, 49%). NMR (400 MHz in CDCl$_3$, Bruker AVANCE-400): δ 1.31 (s, 9H, Boc), 2.90 (m, 2H, CH$_2$), 3.81 (s, 3H, OMe) 4.30 (m, 2H, CH$_2$), 4.33 (m, 1H, CH), 5.12 (s, 2H, OBn), 6.97-7.09 (d, 1H, J=3.5 Hz, Ar—H), 7.15 (d, 1H, J=8.53 Hz, Ar—H), 7.24~7.46 (m, 8H, Ar—H), 7.84, (d, 2H, Ar—H, J=8.24 Hz), 8.24 (br, 1H, NH), 8.43 (br, 1H, NH).

(ii) Synthesis of 4-(3-(5-(benzyloxy)pyridin-2-yl)-2-(tert-Butoxycarbonyl-amino) propanamido)methyl) benzoic acid A mixture of 4-(3-(5-(benzyloxy)pyridin-2-yl)-2-(tert-butoxycarbonylamino)-propanamido)methyl)benzoic acid (1.3 g, 2.58 mmol) and lithium hydroxide (0.6 g, 25 mmol) in 50 mL THF/H$_2$O (1:1) was heated at 60° C. for 4 h (monitored by TLC). The solution was acidified to PH=2 and extracted with dichloromethane. The dichloromethane was evaporated, dried over magnesium sulfate, and concentrated in vacuo to give the title (0.7 g, 55%). NMR (400 MHz in CDCl$_3$, Bruker AVANCE-400): δ 1.31 (s, 9H, Boc) 2.97 (m, 2H, CH$_2$), 4.27 (m, 2H, CH$_2$), 4.33 (m, 1H, CH), 5.13 (s, 2H, OBn), 6.96 (d, 1H, J=8.32 Hz, Ar—H), 7.15-7.18 (m, 3H, Ar—H), 7.31~7.39 (m, 4H, Ar—H), 7.44, (d, 2H, Ar—H, J=7.01 Hz), 7.80 (d, 2H, Ar—H, J=7.67 Hz), 8.24 (br, 1H, NH), 8.43 (br, 1H, NH).

(iii) Synthesis of tert-butyl 3-(5-(benzyloxy)pyridin-2-yl)-1-(4-(hydroxycarbamoyl)benzylamino)-1-oxo-propan-2-ylcarbamate (Compound 7)

4-((3-(5-(Benzyloxy)pyridin-2-yl)-2-(tert-butoxycarbonylamino)propanamido) methylbenzoic (0.65 g 1.25 mmol) in anhydrous THF was added to ethyl chloroformate (0.15 mL, 1.5 mmol) and triethylamine (0.21 mL, 1.88 mmol) at 0° C. The mixture was stirred at 0° C. for 30 min. The solid was removed and the filtrate was added to a hydroxylamine MeOH solution, which was freshly prepared by adding a solution of hydroxylamine hydrochloride (0.14 g, 2.5 mmol) in MeOH (20 mL) to a stirred solution of KOH (0.11 g, 2.5 mmol) in MeOH (10 mL) at 0° C. After stirring for 15 min, the precipitate was removed and the filtrate was stirred at room temperature for 30 min (monitored by TLC) and evaporated in vacuo. The residue was extracted with EA/H$_2$O and recrystallized in CH$_2$Cl$_2$/Ether to give Compound 7 (0.40 g, 61%): mp 106-108° C.; NMR (400 MHz in CDCl$_3$, Bruker AVANCE-400): δ 1.30 (s, 9H, Boc), 2.91 (m, 2H, CH$_2$), 4.26 (m, 2H, CH$_2$), 4.32 (m, 1H, CH), 5.12 (s, 2H, OBn), 6.95 (d, 1H, Ar—H, J=8.24 Hz), 7.14-7.21 (m, 3H, Ar—H), 7.30-7.44 (m, 6H, Ar—H), 7.65 (d, 1H, Ar—H, J=8.38 Hz), 7.8 (d, 1H, Ar—H, J=8.38 Hz), 8.24 (br, 1H, NH), 8.45 (br, 1H, NH), 9.48 (br, 1H, NH), 10.39 (br, 1H, OH).

8. Synthesis of 4-((2-amino-3-(5-(benzyloxy)pyridin-2-yl)-propanamido) methyl)-N-hydroxybenzamide trifluororoacetic acid (Compound 8)

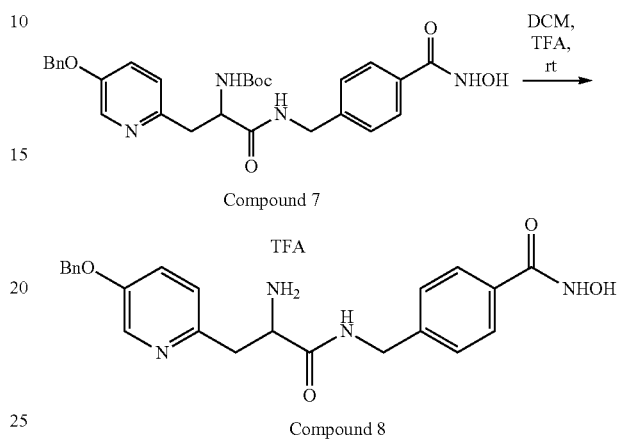

t-Butyl 3-(5-(benzyloxy)pyridin-2-yl)-1-(4-(hydroxylcarbamoyl)benzylamino)-1-oxopropan-2-ylcarbamate (0.26 g, 0.5 mmol) was dissolved in TFA/DCM (v/v=1:1) (30 mL) and stirred for 4 h at room temperature (monitored by TLC). The solution was evaporated with DCM three times to give 0.021 g HPW101x048 (81%): mp 151-154° C.; NMR (400 MHz in CDCl$_3$, Bruker AVANCE-400): δ 3.12 (m, 2H, CH$_2$), 4.25 (m, 2H, CH$_2$), 4.40 (m, 1H, CH), 5.15 (s, 1H, OBn), 7.21 (m, 3H, Ar—H), 7.40 (m, 7H, Ar—H), 7.67 (d, 1H, Ar—H, J=8.21 Hz), 7.84 (d, 1H, Ar—H, J=7.96 Hz), 8.26 (br, 2H, NH$_2$), 8.27 (s, 1H, NH), 8.92 (br, 1H, NH), 11.19 (br, 1H, OH).

9. Synthesis of tert-butyl1-(4-(hydroxycarbamoyl) benzylamino)-3-(5-hydroxypyridin-2-yl)-1-oxopropan-2-ylcarbamate (Compound 9)

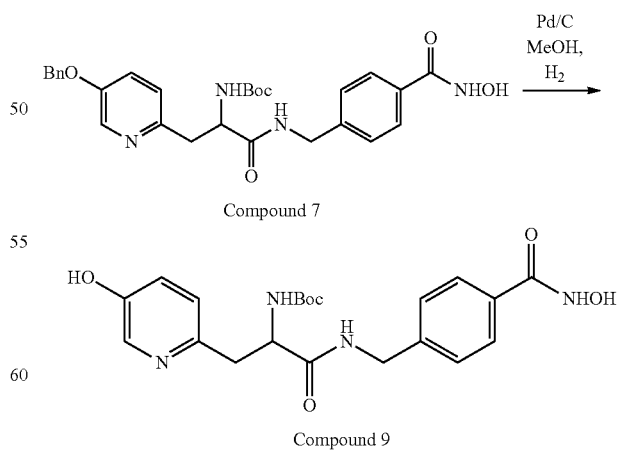

A mixture of t-butyl 3-(5-(benzyloxy)pyridin-2-yl)-1-(4-(hydroxyl-carbamoyl)benzylamino)-1-oxopropan-2-ylcarbamate (Compound 7) (0.26 g, 0.5 mmol) and 26 mg of 10%

Pd/C in 2 mL of methanol was vigorously stirred under H$_2$ for 4 h at room temperature and then filtered through Celite. The solvent was evaporated. The residue was purified by chromatography to give oily Compound 9 (0.16 g, 73%). NMR (400 MHz in CDCl$_3$, Bruker AVANCE-400) δ: 1.28 (s, 9H, Boc), 3.15 (m, 2H, CH$_2$), 4.28 (t, 2H, CH$_2$, J=5.12 Hz), 4.36 (m, 1H, CH), 7.05-7.25 (m, 4H, Ar—H), 7.64-7.84 (m, 3H, Ar—H), 8.23 (br, 1H, NH), 8.51 (br, 1H, NH), 10.18 (br, 1H, NH), 11.16 (br, 1H, OH).

10. Synthesis of 4-((2-amino-3-(5-hydroxypyridin-2-yl)-propanamido) methyl)-N-hydroxybenzamide (Compound 10)

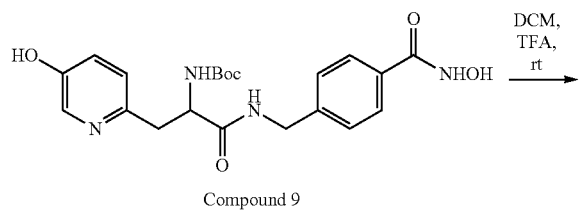

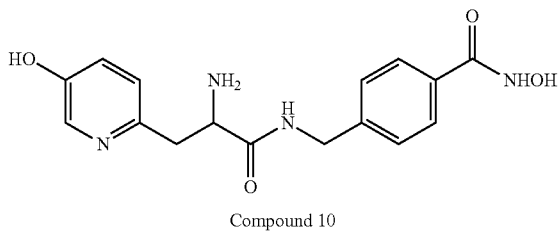

Compound 10

A solution of tert-butyl1-(4-(hydroxycarbamoyl)benzylamino)-3-(5-hydroxypyridin-2-yl)-1-oxopropan-2-ylcarbamate (0.10 g, 0.19 mmol) with 1 mL of TFA in 10 mL of CH$_2$Cl$_2$ (25 mL) was stirred for 4 h at room temperature. The solvent was evaporated (monitored by TLC). The residue was purified by chromatography to give oily Compound 10 (0.045 g, 71%). NMR (400 MHz in CDCl$_3$, Bruker AVANCE-400): δ 3.08 (m, 2H, CH$_2$), 4.20 (m, 2H, CH$_2$), 4.36 (m, 1H, CH), 7.08-7.28 (m, 4H, Ar—H), 7.62-7.70 (m, 2H, Ar—H), 7.82-7.88 (m, 1H, Ar—H), 8.96 (m, 2H, NH$_2$), 9.13 (br, 1H, NH), 9.97 (br, 1H, NH), 11.15 (br, 1H, OH).

11. Synthesis of (R)-4-(4-(hydroxyamino)-4-oxobutyl)phenyl-3-(5-(benzyloxy)pyridin-2-yl)-2-(tert-butoxycarbonylamino)propanoate (Compound 11)

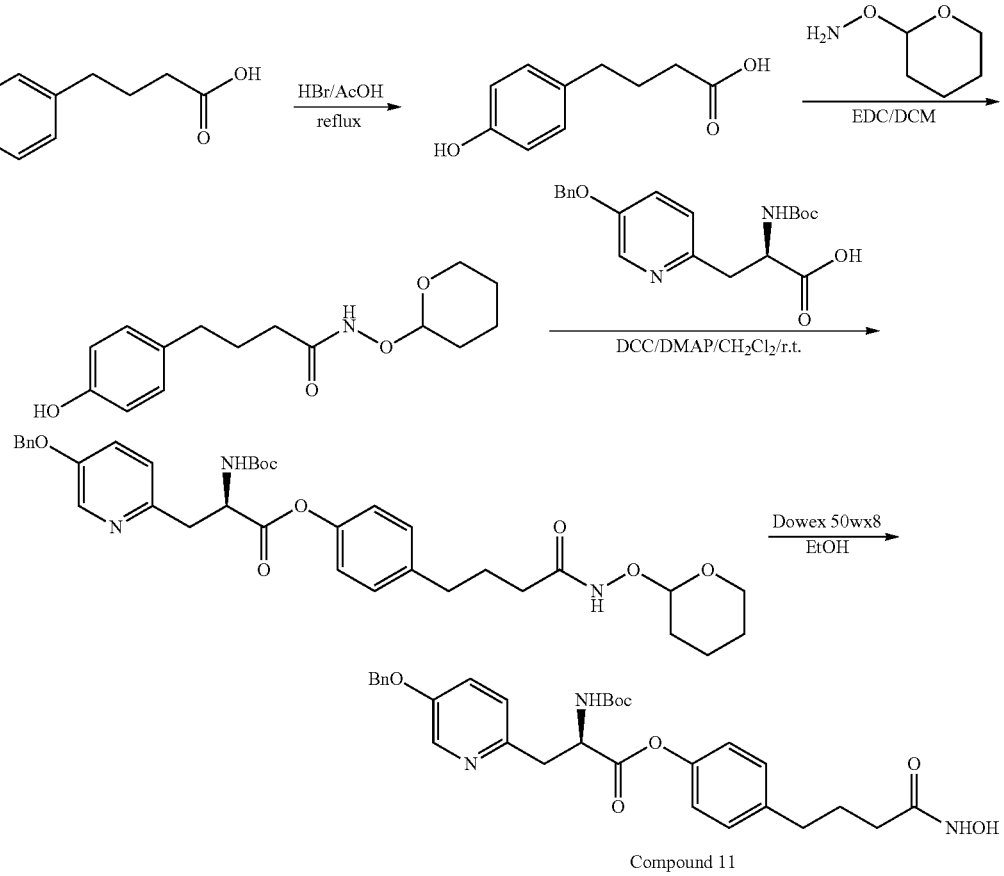

Compound 11

(i) Synthesis of 4-(4-hydroxyphenyl)butanoic acid 4-(4-Methoxyphenyl)butanoic acid (0.97 g, 5 mmol) was mixed with HBr (50 mL) and acetic acid galacial (80 mL). The mixture was refluxed for 12 h (monitored by TLC), poured into ice, stirred for 1 h, and then extracted with DCM. The solvent was evaporated in vacuo to give the title compound (0.83 g, 92%). NMR (400 MHz in CDCl$_3$, Bruker AVANCE-400): δ 1.72 (m, 2H, CH$_2$), 2.16 (t, 2H, CH$_2$, J=7.4 Hz), 2.45 (t, 2H, CH$_2$, J=7.6 Hz), 6.65 (d, 2H, Ar—H, J=8.3 Hz), 6.95 (d, 2H, Ar—H, J=8.3 Hz).

(ii) Synthesis of 4-(4-hydroxyphenyl)-N-(tetrahydro-2H-pyran-2-yloxy)butanamide A mixture of 4-(4-Hydroxyphenyl)butanoic acid (0.90 g, 5 mmol), O-(tetrahydro-2H-pyran-2-yl)hydroxylamine (0.59 g, 5 mmol) and 1-ethyl-3-(3-dimethyllaminopropyl)carbodiimide hydrochloride (1.15 g, 6 mmol) in 50 mL dichloromethane was stirred at room temperature for 2 h (monitored by TLC). The mixture was extracted with water and dried over magnesium sulfate. The residue was purified by chromatography (MeOH:DCM=1:50) to give the title compound (0.84 g, 65%). NMR (400 MHz in DMSO, Bruker AVANCE-400): δ 1.50 (m, 3H, OTHP), 1.71 (m, 3H, OTHP), 1.73 (m, 2H, CH$_2$), 1.96 (m, 2H, CH$_2$), 2.44 (m, 2H, CH$_2$), 3.48 (t, 1H, J=5.0 Hz, OTHP), 3.91 (t, 1H, J=10.0 Hz, OTHP), 4.80 (s, 1H, OTHP), 6.65 (d, 2H, J=5.0 Hz, Ar—H), 6.95 (d, 2H, J=10.0 Hz, Ar—H), 9.10 (s, 1H, NH), 10.87 (s, 1H, OH).

(iii) Synthesis of (2R)-4-(4-oxo-4-(tetrahydro-2H-pyran-2-yloxyamino)butyl)phenyl 3-(5-(benzyloxy)pyridin-2-yl)-2-(tert-butoxycarbonylamino)propanoate (R)-3-(5-(Benzyloxy)pyridin-2-yl)-2-(tert-butoxycarbonylamino)propanoic acid (0.19 g, 0.5 mmol), 4-(4-hydroxyphenyl)-N-(tetrahydro-2H-pyran-2-yloxy)-butanamide (0.14 g, 0.5 mmol), and DMAP (0.06 g, 0.5 mmol) were added into DCM (10 mL) and stirred at 0° C. for 10 min. A solution of DCC (0.12 g, 0.6 mmol) in DCM (5 mL) was added to the above-mentioned solution dropwise. The mixture was stirred from 0° C. at room temperature for 1 h (monitored by TLC). The white solid was removed and the filtrated was then evaporated in vacuo. Ethyl acetoacetate was added and the solid was again removed. The solution was evaporated in vacuo. The residue was purified by chromatography (EA:Hex=1:5) to give the title compound.

(iv) Synthesis of (R)-4-(4-(hydroxyamino)-4-oxobutyl)phenyl-3-(5-(benzyloxy)pyridin-2-yl)-2-(tert-butoxycarbonylamino)propanoate (Compound 11)

A mixture of (2R)-4-(4-oxo-4-(tetrahydro-2H-pyran-2-yloxyamino)butyl)phenyl 3-(5-(benzyloxy)pyridin-2-yl)-2-(tert-butoxycarbonylamino)propanoate (0.32 g, 0.5 mmol) and Dowex 50wX8 (0.5 mmol) in ethanol (2.5 mL) was refluxed 1 h (monitored by TLC). The precipitate was removed and the filtrate was evaporated in vacuo. The residue was purified by chromatography (MeOH:DCM=1:25) to give the title compound.

12. Synthesis of (R)-4-(hydroxycarbamoyl)benzyl 3-(5-(benzyloxy)-pyridin-2-yl)-2-(tert-butoxycarbonylamino)propanoate (Compound 15)

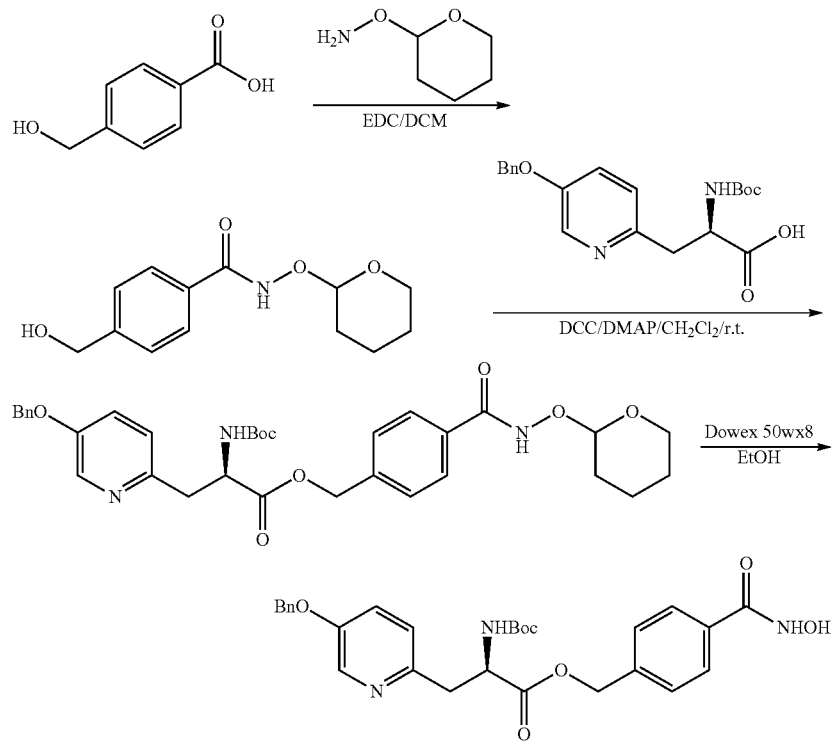

Compound 15

(i) Synthesis of 4-(hydroxymethyl)-N-(tetrahydro-2H-pyran-2-yloxy)benzamide

A mixture of 4-(Hydroxymethyl)benzoic acid (0.75 g, 5 mmol), O-(tetrahydro-2H-pyran-2-yl)hydroxylamine (0.59 g, 5 mmol), and 1-ethyl-3-(3-dimethylaminopropyl)carbodiimide hydrochloride (1.15 g, 6 mmol) in dichloromethane (50 mL) was stirred at room temperature for 2 h (monitored by TLC). The mixture was extracted with water and dried over magnesium sulfate. The residue was purified by chromatography (MeOH:DCM=1:50) to give the title compound (0.88 g, 70%). NMR (400 MHz in DMSO, Bruker AVANCE-400): δ 1.52 (m, 3H, OTHP), 1.72 (m, 3H, OTHP), 3.51 (m, 1H, OTHP), 4.04 (m, 1H, OTHP), 4.53 (s, 2H, $CH_2$), 4.98 (s, 1H, OTHP), 5.28 (s, 1H, NH), 7.38 (d, 2H, J=10.0 Hz, Ar—H), 7.72 (d, 2H, J=5.0 Hz, Ar—H), 11.55 (s, 1H, OH).

(ii) Synthesis of (2R)-4-(tetrahydro-2H-pyran-2-yloxycarbamoyl)benzyl 345-(benzyloxy)pyridin-2-yl)-2-(tert-butoxycarbonylamino)propanoate (R)-3-(5-(Benzyloxy)pyridin-2-yl)-2-(tert-butoxycarbonylamino)propanoic acid (0.19 g, 0.5 mmol), 4-(hydroxymethyl)-N-(tetrahydro-2H-pyran-2-yloxy)-benzamide (0.13 g, 0.5 mmol), and DMAP (0.06 g, 0.5 mmol) were added into DCM (10 mL) stirred at 0° C. for 10 min. DCC (0.12 g, 0.6 mmol) was dissolved in DCM (5 mL) and then added to the above-mentioned solution slowly. The mixture was stirred from 0° C. to room temperature 1 h (monitored by TLC). The white solid was filtered off and the filtrate was then evaporated in vacuo. The residue was purified by chromatography (MeOH:DCM=1:50) to give the title compound (0.18 g, 60%). NMR (400 MHz in DMSO, Bruker AVANCE-400): δ 1.32 (s, 9H, Boc), 1.59 (m, 3H, OTHP), 1.70 (m, 3H, OTHP), 3.0 (m, 2H, $CH_2$), 3.50 (d, 1H, J=10.0 Hz, OTHP), 4.04 (br, 1H, OTHP), 4.44 (m, 1H, CH), 4.98 (s, 1H, OTHP), 5.12 (s, 4H, OBn and $C(O)OCH_2$), 5.54 (s, 1H, NH), 5.55 (s, 1H, NH), 7.16 (d, 1H, J=10.0 Hz, Ar—H), 7.28-7.39 (m, 7H, Ar—H), 7.44 (d, 2H, J=5.0 Hz, Ar—H), 7.72 (d, 2H, J=5.0 Hz, Ar—H), 8.24 (s, 1H, Ar—H).

(iii) Synthesis of (R)-4-(hydroxycarbamoyl)benzyl 3-(5-(benzyloxy)pyridin-2-yl)-2-(tert-butoxycarbonylamino)propanoate (Compound 15)

A mixture of (2R)-4-(tetrahydro-2H-pyran-2-yloxycarbamoyl)benzyl 345-(benzyloxy)pyridin-2-yl)-2-(tert-butoxycarbonylamino)propanoate (0.30 g, 0.5 mmol) and Dowex 50wX8 (0.5 mmol) in ethanol (2.5 mL) was refluxed for 1 h (monitored by TLC). The precipitate was removed and the filtrate was evaporated in vacuo. The residue was purified by chromatography (MeOH:DCM=1:25) to give compound 15.

Example 2

Bioassays

1. HDAC Inhibition Assay

The histone deacetylase (HDAC) activity was measured in HeLa lysate suspensions using a Fluor de Lys™ fluorescent assay system (Biomol, Enzo Life Sciences; PA, USA) with some modification as described previously (Pflum et al., 2007). In brief, HeLa lysate (1.5 µl) were preincubated in the presence of test compound or vehicle (DMSO, 0.2% v/v) at 30° C. for 10 minutes, therefore Fluor de Lys™ substrate (125 µM) was added and incubated at 37° C. under shaking for 45 minutes. Finally, the developer reagent (95 µl, 1×) was immediately added to the same aliquot of the reaction mixture for another 10 minutes. The extent of deacetylated substrate formation was monitored by a microplate fluorescence reader (Thermo Varioskan Flash, Thermofisher; MA, USA) to determine the fluorescence intensity (excitation at 360 nm, emission at 460 nm). The results were expressed as the percent inhibition of the rate of deacetylated substrate formation on the reacting interval. SAHA (10 µM), as a classical HDACi, was used as a positive control. See Bieliauskas et al., *Bioorg. Med. Chem. Lett.*, 2007, 17: 2216-2219.

Compounds 1-8 were tested. All of them showed HDAC inhibitory activities at the concentration of $10^{-5}$ M or even lower. The dose-dependent inhibition of HDAC was determined for Compounds 3, 4, and 7 and SAHA and $IC_{50}$ values were shown in the following table.

TABLE 1

| | $IC_{50}$ of HDAC inhibition | | | | |
|---|---|---|---|---|---|
| Compound | 1 | 3 | 4 | 7 | SAHA |
| $IC_{50}$ | $1.73 \times 10^{-5}$ M | $3.98 \times 10^{-7}$ M | $4.13 \times 10^{-6}$ M | $1.32 \times 10^{-6}$ M | $3.98 \times 10^{-7}$ M |

2. In Vitro Wound Healing Activity

The wound healing activities of Compounds 1 and 3 were in vitro assessed by the method provided in Valster et al., Methods, 2005, 37, 208-215 and Rodriguez et al., "Methods in Molecular Biology" in Cell Migration: Developmental Methods and Protocols, vol. 294, Ed by Guan et al. Humana. Press Inc.

IMR90 cells were seeded on a six-well culture dish and grown in MEM medium with 10% FBS to confluence in the presence of serum. The growth medium (MEM with 10% FBS) was then replaced with a serum-free medium (MEM without FBS). After starved for 24 hours, wounds were made by scraping using a P1000 pipette tip. The cells were treated with Compound 1 (0, 0.1, 0.5, or 1 mM) or Compound 3 (0, 0.05, 0.5, or 1 µM) for 24 hours. The wounds were observed by a phase contrast microscopy using an inverted microscope. Images were taken at areas flanking the intersections of the wounds and the marker lines at regular intervals over a period of 24 hours. These images were analyzed through a digital imaging system using Image-Pro Plus® (Media Cybernetics, Silver Spring, Md.) to determine the position of the migrating cells at the wound edges. The cell migration distance was calculated by substracting the width of the wound at each interval from its initial width.

The results showed that both Compound 1 and 3 promoted wound healing.

3. In Vitro COX-2 Protein Expression

To detect COX-2 protein expression, Western blot analysis was performed as follows. Briefly, Compound 3-treated IMR90 cells, stimulated by wounds (scraping using a P1000 pipette tip) and non-stimulated, were collected and lysed in 1× lysis buffer. Protein concentrations of these lysed cells were measured using Bio-Rad quantification assay (Bio-Rad Laboratory, CA). Protein extracts (20 µg) were subjected to electrophoresis on a 10% SDS-PAGE and transferred to PVDF membrane. The antibody recognizing COX-2 was obtained from Epitomics (Burlingame, Calif.). The antibody recognizing β-actin was from obtained Sigma (St. Louis, Mo.). All antibodies were rabbit polyclonal antibodies except for the β-actin antibody, which was a mouse monoclonal antibody. Secondary antibodies were anti-rabbit IgG and anti-mouse IgG (horseradish-peroxidase linked antibodies), respectively (Amersham Biosciences, Piscataway, N.J.). Primary antibodies were used at a 1:1,000 dilution and secondary antibodies were used at a 1:5,000 dilution in a solution containing 5% BSA in TBS-T. Immunoreactive proteins were detected using the enhanced chemiluminescence light (ECL) detecting kit (Millipore).

The results showed that Compound 3 inhibited COX-2 protein expression in the range between 0.05-1.0 μM in a dose-dependent manner.

4. In Vitro Acetyl-H3 Protein Expression

Acetyl-H3 protein expression was also detected using Western blot analysis. Briefly, IMR90 cells were treated with Compounds 1-4 and lysed in the manner described in Sections 2 and 3. Acetyl-H3 protein was detected by primary antibodies and secondary antibodies. The polyclonal antibody against acetyl-H3 protein was obtained from Santa Cruz Biotechnology (Santa Cruz, Calif.). The monoclonal antibody recognizing β-actin was obtained from ICN (Costa Mesa, Calif.). Secondary antibodies were anti-rabbit IgG and anti-mouse IgG (horseradish-peroxidase linked antibodies), respectively (Amersham Biosciences, Piscataway, N.J.). All antibodies were used at a 1:1,000 dilution in a solution containing 5% milk in TBS-T. Immunoreactive proteins were detected using the enhanced chemiluminescence light (ECL) detecting kit (Amersham Biosciences).

The results showed that Compounds 1-4 promoted acetyl-H3 protein induction in IMR90 cells.

5. In Vivo Anti-Mucositis Activity

Twenty young Syrian golden hamsters, 7 to 8 weeks old weighing 90 to 130 g, were numbered and randomly divided into five groups (4 hamsters each group).

Each hamster in the five groups was punched at the right buccal pouch mucosa with a skin puncher on Day 0 to give a 6 mm diameter wound. Four groups were intraperitoneally administered with 5-FU at 20 mg/kg twice at Day 0 and one group was used as a control without any treatment. Among the four 5-FU treated groups, three were subcutaneously administered with Compound 1 at 36, 72, and 144 mg/kg or Compound 3 at 0.5, 5.0 and 50.0 mg/kg once a day from Day 0 to Day 5. Wounds were examined macroscopically and microscopically 0.5, 1, 2, 3, 4, 5, and 6 days after the punching. The hematological parameters, serum biochemistry, extents of inflammatory cell infiltration, sizes of hemorrhagic areas, and presence of ulcers and abscesses were recorded. After Day 6, all of the hamsters were anesthetized with isoflurane (2-chloro-2-difluoromethoxy-1,1,1-trifluoro-ethane) for macroscopic and histological analysis and Western blot analysis.

The results showed that both Compounds 1 and 3 reduced 5-FU-induced mucositis in wound areas in a dose-dependent manner.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of the following formula:

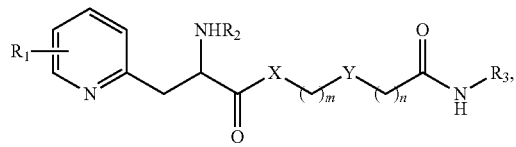

wherein $R_1$ is H, OH, amino, alkoxy, arylalkoxy, alkylcarbonyloxy, or alkoxycarbonyloxy; $R_2$ is H, OH, alkoxy, alkylcarbonyl, or alkoxycarbonyl; $R_3$ is OH or phenyl; X is O or NH; Y is phenylene or —$CH_2$—; and each of m and n, independently, is 0, 1, 2, 3, 4, or 5, provided that when X is O, Y is phenylene or —$CH_2$—, and that when X is NH, Y is phenylene.

2. The compound of claim 1, wherein X is NH.
3. The compound of claim 2, wherein m is 0 and n is 3.
4. The compound of claim 3, wherein $R_3$ is OH.
5. The compound of claim 1, wherein $R_3$ is OH.
6. The compound of claim 1, wherein X is O.
7. The compound of claim 1, wherein $R_1$ is OH or alkoxy.
8. The compound of claim 1, wherein $R_1$ is benzyloxy.
9. The compound of claim 1, wherein the compound is selected from the group consisting of the following compounds:

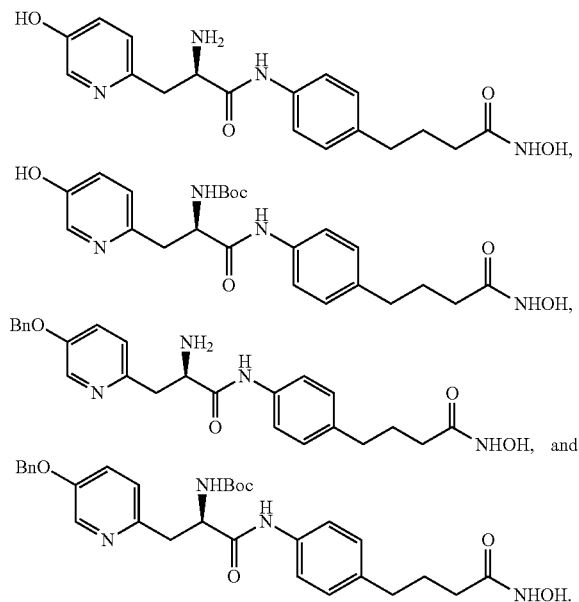

10. A method of treating mucositis, comprising administering to a subject in need thereof an effective amount of the compound of claim 1.
11. A method for treating cancer, comprising administering to a subject in need thereof an effective amount of a compound of claim 1.
12. The method of claim 10, wherein the compound is a compound of claim 2.
13. The method of claim 10, wherein the compound is a compound of claim 4.
14. The method of claim 10, wherein the compound is a compound of claim 5.
15. The method of claim 10, wherein the compound is a compound of claim 7.

16. The method of claim 10, wherein the compound is a compound of claim 8.

17. The method of claim 10, wherein the compound is a compound of claim 9.

18. The method of claim 11, wherein the compound is a compound of claim 2.

19. The method of claim 11, wherein the compound is a compound of claim 4.

20. The method of claim 11, wherein the compound is a compound of claim 5.

21. The method of claim 11, wherein the compound is a compound of claim 7.

22. The method of claim 11, wherein the compound is a compound of claim 8.

23. The method of claim 11, wherein the compound is a compound of claim 9.

* * * * *